United States Patent [19]

Takagi et al.

[11] Patent Number: 4,504,471

[45] Date of Patent: Mar. 12, 1985

[54] ANIMAL GROWTH PROMOTANT AND METHOD OF USE FOR ANIMAL GROWTH

[75] Inventors: Hirofumi Takagi; Kiyohiko Kunugita; Hideki Sawai, all of Sakura; Kazuo Kariyone, Kyoto, all of Japan

[73] Assignee: Fujisawa Pharmaceutical Co., Ltd., Osaka, Japan

[21] Appl. No.: 529,680

[22] Filed: Sep. 6, 1983

[30] Foreign Application Priority Data

Sep. 27, 1982 [GB] United Kingdom ............... 8227513

[51] Int. Cl.³ ............................................. A61K 37/02
[52] U.S. Cl. ...................................................... 514/18
[58] Field of Search ........................................ 424/177

[56] References Cited

U.S. PATENT DOCUMENTS 4,322,341 3/1982 Kitaura et al. .

Primary Examiner—Delbert R. Phillips
Assistant Examiner—F. T. Moezie
Attorney, Agent, or Firm—Oblon, Fisher, Spivak, McClelland & Maier

[57] ABSTRACT

This invention relates to a new animal growth promotant which comprises an acyl peptide or its non-toxic salt as an active ingredient. In addition, this invention also relates to a method for promoting the growth of animals, to a method of improving the rate of weight gain of animals, and to a method of improving the efficiency of feed utilization by animals which comprises administering orally the animal growth promotant and a suitable carrier or animal feed to animals.

14 Claims, No Drawings

ANIMAL GROWTH PROMOTANT AND METHOD OF USE FOR ANIMAL GROWTH

BACKGROUND OF THE INVENTION

1. Field of the Invention

This invention relates to a new animal growth promotant. More particularly, it relates to a new animal feed composition which comprises an acyl peptide or its non-toxic salt as an effective ingredient, and to methods for promoting the growth of animals and improving the rate of weight gain of animals and improving the efficiency of feed utilization by animals, which comprises the oral administration of the animal feed composition comprising the acyl peptide or its non-toxic salt to animals.

2. Description of the Prior Art

The acyl peptide to be used in this invention is represented by the following formula (I).

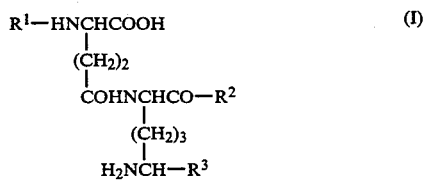

wherein
$R^1$ is lactoyl-alanyl-, $R^2$ is carboxymethylamino, and $R^3$ is carboxy; or
$R^1$ is heptanoyl, $R^2$ is 1-carboxyethylamino and $R^3$ is carboxy; or
$R^1$ is stearoyl, $R^2$ is 1-carboxyethylamino and $R^3$ is hydrogen.

The acyl peptide (I) and its non-toxic salt to be used in this invention is the known one possessing an enhancing activity of immune response [cf. U.S. Pat. No. 4322341].

For many years, the animal science industry has tried to provide an animal growth promotant, and some antibiotics have been developed and used as such, including, for example, penicillins, tetracyclines, bacitracin, enramycin, virginiamycin or the like. The antibiotics used as animal growth promotants up to now are characterized by their strong antimicrobial activities, especially against Gram-positive bacteria. Accordingly, it has been a matter of common knowledge in the field of animal science that when an antibiotic is used as an animal growth promotant, the antibiotic may be preferably selected from the ones which possess antimicrobial activities, especially against Gram-positive bacteria.

However, the animal growth promotants available in the market, including such antibiotics, can not be said to be entirely sufficient in the actual application thereof to animals due to the occurrence of antibiotic resistant microorganisms and the like.

DESCRIPTION OF THE EMBODIMENTS

The acyl peptide (I) is inactive against microorganisms in vitro, although it possesses an enhancing activity of the immune response and protective efficacy in experimental infection.

Accordingly, if the acyl peptide (I) possessing such unique pharmacological properties can effectively be used as an animal growth promotant, an actually useful animal growth promotant which is not accompanied with occurrence of antibiotic-resistant microorganisms, can be provided.

On the basis of these facts, the inventors of this invention have studied a possibility of the effective use of the acyl peptide (I) as an animal growth promotant for animals (e.g. chicken, pig, etc.).

The extensive studies of the inventors have successfully resulted in providing a new animal growth promotant comprising the acyl peptide (I) or its non-toxic salt.

Accordingly, this invention provides a new animal feed composition for promoting the growth of animals, which comprises the acyl peptide (I) or its non-toxic salt as an effective ingredient; and methods for promoting the growth of animals, improving the rate of weight gain of animals, and improving the efficiency of feed utilization by animals, this invention encompasses the oral administration of the animal feed composition comprising the acyl peptide (I) or its non-toxic salt to animals.

A non-toxic salt of the acyl peptide (I) may include a salt formed with an inorganic or organic base such as a sodium salt, potassium salt, calcium salt, ammonium salt, ethanolamine salt, triethylamine salt, dicyclohexylamine salt and the like, and an acid addition salt with an organic or inorganic acid such as acetate, trifluoroacetate, lactate, maleate, fumarate, tartarate, citrate, methane sulfonate, hydrochloride, sulfate, nitrate, phosphate and the like.

The acyl peptide (I) to be used in this invention, includes one or more stereoisomers due to the asymmetric carbon atoms in the molecule, and all of such isomers are included within the scope of the active ingredient of this invention.

Representative compounds of the acyl peptide (I) to be used in this invention are as follows:

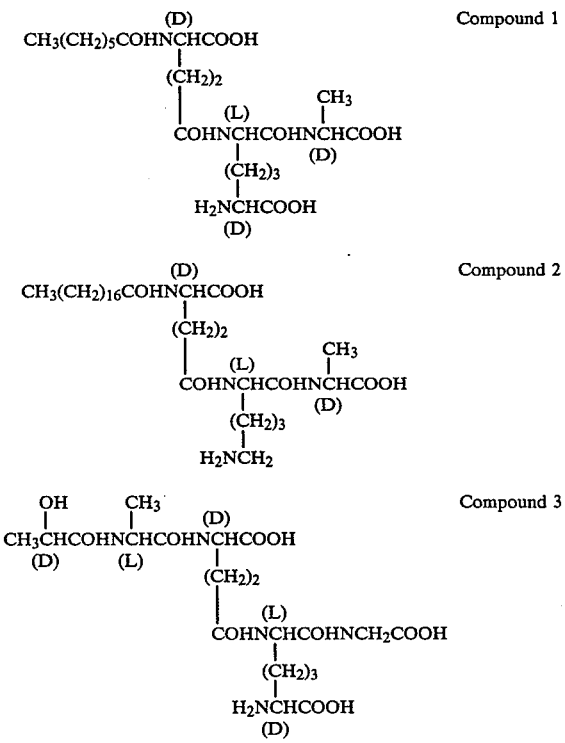

The animal growth promotant of this invention which comprises the acyl peptide (I) or its non-toxic salt as an effective ingredient is administered to animals in a conventional manner.

The animal growth promotant of this invention is usually administered orally to animals, and the active ingredient, the acyl peptide (I) or its non-toxic salt, may be generally administered as it is or in admixture with a suitable carrier (e.g., water, kaolin, talc, calcium carbonate, lactose, etc.) or in admixture with an animal nutritions source, i.e., feed.

More particularly, the active ingredient, the acyl peptide (I) or its non-toxic salt, may also be administered as drinking water in the form of an aqueous solution; or as a preparation such as tablet, granule or capsule which comprises the acyl peptide (I) or its non-toxic salt and suitable non-toxic carrier as exemplified above; or as a ration in the form of the composition which comprises the acyl peptide (I) or its non-toxic salt and animal feed and sometimes the other feed additive.

In connection with the form of administering the animal feed composition of this invention as mentioned above, the ration comprising the acyl peptide (I) or its non-toxic salt can be prepared in a conventional manner, namely by admixing the acyl peptide (I) or its non-toxic salt with basal ration. And, as the basal ration, natural feed and assorted feed can be used, including dry feeds, liquid feed, pelleted feed and the like. As a preferred basal ration, it is preferably used the assorted feed which comprises one or more conventional feeds such as corn, rice, wheat, milo, soybean meal, cottonseed meal, wheat bran, defatted rice bran, fish meal, skim milk, dried whey, oils, fats, alfalfa meal or the like and one or more of the conventional feed additives such as tricalcium carbonate, sodium chloride, choline chloride, vitamin (e.g. vitamin A, vitamin D, vitamin E, vitamin $B_1$, vitamin $B_2$, vitamin $B_6$, vitamin $B_{12}$, calcium pantothenate, nicotinamide, folic acid, etc.), amino acid (e.g. lysine, methionine, etc.), mineral source (e.g. magnesium sulfate, ferrous sulfate, copper sulfate, zinc sulfate, potassium iodide, cobalt sulfate, etc.) or the like.

The amounts of the acyl peptide (I) or its non-toxic salt in the basal rations which are fed to the animals may be varied over a very wide range depending upon the kind, nature, growth period, etc. of the animals, and the breeding method, breeding circumstance, breeding seasons of the animals and the like. Levels which are construed as preferable and anticipated to yield the preferred growth are in an amount between about 0.01 p.p.m. and about 100 p.p.m., more preferably between about 0.1 p.p.m. and about 10 p.p.m.

As to the other form of administration, the capsules can be prepared by filling the acyl peptide (I) or its non-toxic salt. If desired, the acyl peptide (I) or its non-toxic salt is diluted with an inert powdered diluent (e.g. sugar, starch, cellulose, etc.) in a conventional manner in order to increase its volume for convenience in filling capsules. The tablet can be prepared in a conventional manner, for example, by admixing the acyl peptide (I) or its non-toxic salt with a base (e.g. lactose, sugar, mannitol, starch, sodium chloride, etc.), a disintegrator (e.g. starch, alginic acid, sodium lauryl sulfate, etc.), a binder (e.g. gelatin, gums, starch, dextrin, etc.), a lubricant (magnesium stearate, talc, paraffin wax, polyethylene glycol, etc.). The granules also can be prepared in a conventional manner. The drinking water comprising the acyl peptide (I) or its non-toxic salt can be prepared by simply dissolving the acyl peptide (I) or its non-toxic salt in water in a proper amount.

The dosage of the animal feed composition is varied depending upon the kind, nature, growth period, etc. of the animals, and its preferred dosage may usually be selected from the range of about 0.01–10 mg/kg/day as the amount of the acyl peptide (I) or its non-toxic salt.

Further, the animal feed composition as prepared above can also include, other feed additives than those mentioned above, for example, other antibiotics, pesticides, fungicides, coccidiostats, antioxidants, natural pigments and the like. A preferred antibiotic to be added is exemplified by thiopeptin, enramycin, bacitracin, mikamycin, fradiomycin, flavomycin, virginiamycin, kitasamycin, tylosin, quebemycin and the like, which are useful as animal growth promotants and/or veterinary drugs. Furthermore, it is usual to treat animals with a variety of growth promotants, disease-preventatives and disease treatments throughout their lives, and such drugs are often used in combination. Accordingly, the new methods of this invention may also be practiced in combination with other treatments.

The animal growth promotant of this invention can be administered effectively to animals such as poultry (e.g. chicken, turkey, duck, quail, etc.), cattle, pig, sheep, goat, rabbit, mink and the like. The breeding of animals using the animal feed composition of this invention can be conducted in a conventional manner.

The animal growth promotant of this invention promotes the growth of animals so that the rate of weight gain of animal can be improved, and also improves the efficiency of feed utilization by animals. In addition to this, the animal growth promotant of this invention is superior to other grow the promotants in that the animal growth promotant of this invention is not accompanied by the occurrence of antibiotic-resistant microorganisms.

From the uses and advantages stated above, the animal growth promotant of this invention can be said to be a superior animal promotant in comparison with the other known growth promotants and therefore can be used safely for promoting the growth of animals.

The following Tests and Examples are given to illustrate this invention, but is should be understood that they are not intended to limit this invention.

Test 1

7-Days-old male broiler chickens (Chunky) were divided into two groups, i.e. treatment group and control group, each of which consisted of four chicks. These chicks were fed for initial 4 weeks with Feed Composition I and for further 4 weeks Feed Composition II as listed in the table below.

The said Feed Compositions were continuously fed to the chickens, and their growth and the efficiency of feed utilization by the chickens were observed for 8 weeks.

The results are shown in the table below.

| Ingredient (%) | Feed Composition | |
| --- | --- | --- |
| | Composition | |
| | Feed Composition I | Feed Composition II |
| Corn | 51.40 | 54.60 |
| Milo | 14.00 | 20.00 |
| Soybean meal | 20.00 | 14.00 |
| Fish meal | 8.00 | 5.00 |
| Alfalfa meal | 3.00 | 3.00 |
| Calcium carbonate | 1.50 | 1.50 |
| Tricalcium phosphate | 1.00 | 1.00 |
| Sodium chloride | 0.50 | 0.45 |

Feed Composition

| Ingredient (%) | Feed Composition I | Feed Composition II |
|---|---|---|
| Vitamin A D$_3$ E premix | 0.10 | 0.10 |
| Vitamin B premix*[1] | 0.20 | 0.20 |
| Trace mineral premix*[2] | 0.10 | 0.05 |
| DL-Methionine | 0.20 | 0.10 |
| Compound 1 | 1 ppm | 1 ppm |

Note:
*[1] Vitamin B premix is composed of vitamin B$_1$, vitamin B$_2$, vitamin B$_6$, vitamin B$_{12}$, biotin, folic acid and calcium pantothenate.
*[2] Trace mineral premix is composed of ferrous sulfate, manganese sulfate, zinc sulfate, copper sulfate, cobalt sulfate and potassium iodide.

|  | Initial | 0–1 | 0–2 | 0–3 | 0–4 | 0–5 | 0–6 | 0–7 | 0–8 |
|---|---|---|---|---|---|---|---|---|---|
| (1) Average body weight gain (g): | | | | | | | | | |
| Treatment Group | 116 | 155 (116) | 453 (111) | 783 (107) | 1143 (102) | 1529 (102) | 1977 (105) | 2359 (105) | 2784 (107) |
| Control | 111 | 134 | 407 | 729 | 1120 | 1494 | 1889 | 2238 | 2595 |
| (2) Efficiency of feed utilization*: | | | | | | | | | |
| Treatment Group | | 1.87 (78) | 1.72 (90) | 1.73 (97) | 1.87 (98) | 2.02 (96) | 2.13 (97) | 2.31 (97) | 2.42 (96) |
| Control | | 2.39 | 1.91 | 1.78 | 1.91 | 2.10 | 2.20 | 2.38 | 2.51 |

Values in parentheses represent an index (%) to the control group.
*Note:
$$\text{Efficiency of feed utilization} = \frac{\text{Feed Compositions (g) utilized}}{\text{Average body weight gain (g)}}$$

Test 2

63 Days-old piglets (LWD) were divided into two groups (i.e. treatment group and control group, each of which consisted of four piglets. These piglets were continuously fed for initial 4 weeks with Feed Composition I as shown in the table below and for further 4 weeks with Feed Composition II as shown in the table below, and their growth and efficiency of feed utilization were observed for 8 weeks.

The results are shown in the following table.

Feed Composition

| Ingredient | Feed Composition I (%) | Feed Composition II (%) |
|---|---|---|
| Corn | 62.15 | 37.5 |
| Milo | — | 28.5 |
| Parched bean flour | 7.0 | — |
| Soybean meal | 10.0 | 12.0 |
| Barley | — | 8.0 |
| Skim milk | 10.0 | — |
| Fish meal | 5.0 | 4.6 |
| Glucose | 4.0 | — |
| Bran | — | 6.0 |
| Meat and bone scraps | — | 2.0 |
| Tricalcium phosphate | 1.0 | 0.35 |
| Calcium carbonate | 0.3 | — |
| Sodium chloride | 0.25 | 0.4 |
| DL-Methionine | — | 0.05 |
| Lysine hydrochloride | 0.1 | — |
| Limestone ground | — | 0.6 |
| Vitamin AD$_3$E premix | 0.2 | 0.2 |
| Vitamin B premix*[1] | 0.2 | 0.2 |
| Trace mineral premix | 0.1 | 0.1 |
| Combinase (cellulase + protease) | 0.2 | — |
| Compound 1 | 1, 10 or 100 ppm | 1, 10 or 100 ppm |

Note:
*[1] and *[2]: See Test 1.

|  | Control | Treatment Group Compound 1 | | |
|---|---|---|---|---|
|  |  | 1 ppm | 10 ppm | 100 ppm |
| Average Final Body Weight Gain (kg) | 34.7 | 40.3 (116) | 34.7 (100) | 37.8 (109) |
| Efficiency of Feed Utilization | 2.43 | 2.38 (98) | 2.35 (97) | 2.27 (93) |

Values in parentheses represent an index (%) to the control group.
Note:
$$\text{Efficiency of feed utilization} = \frac{\text{Feed Compositions (kg) utilized for 8 weeks duration}}{\text{Average body weight gain (kg)}}$$

Test 3

The test was conducted by the same method as that of Test 1 excepting the following conditions.

Animals to be used: 6 day-old male broiler chickens. Treatment Groups 1 and 2, and Control Group were each consisted of five chickens.

Effective ingredient to be used in Feed Composition: Compound 2 (Treatment Group 1) and Compound 3 (Treatment Group 2).

The test results are shown in the following table.

|  | Initial | Week 0–2 | Week 0–4 | Week 0–6 |
|---|---|---|---|---|
| (1) Average body weight gain (g): | | | | |
| Treatment Group 1 | 92 | 391 (117) | 997 (109) | 1725 (104) |
| Treatment Group 2 | 91 | 368 (110) | 1006 (110) | 1762 (106) |
| Control | 91 | 335 (100) | 913 (100) | 1659 (100) |
| (2) Efficiency of feed utilization: | | | | |
| Treatment Group 1 | | 1.76 (93) | 1.94 (80) | 2.26 (95) |
| Treatment Group 2 | | 2.09 (93) | 2.06 (85) | 2.26 (95) |
| Control | | 2.24 (100) | 2.41 (100) | 2.37 (100) |

Values in parentheses represent an index (%) to the control group.

Test 4

The test was conducted by the same method as that of Test 2 excepting that the compound 2 (1 ppm) was employed as an effective ingredient in Feed Composition instead of the compound 1.

The results are shown in the following table.

|  | Control | Treatment Group |
|---|---|---|
| Average Final Body Weight Gain (kg) | 28.3 (100) | 29.4 (104) |
| Efficiency of Feed Utilization | 2.30 (100) | 2.28 (99) |

Values in parentheses represent an index (%) to the control group.

EXAMPLE 1

| Ingredient | |
| --- | --- |
| Corn | 601 kg |
| Defatted soybean | 250 kg |
| Alfalfa meal | 20 kg |
| Fish meal | 80 kg |
| Plant oil | 25 kg |
| Calcium carbonate | 10 kg |
| Tricalcium phosphate | 5 kg |
| Sodium chloride | 3 kg |
| Vitamin A D$_3$ E premix | 1 kg |
| Vitamin B premix*[1] | 3 kg |
| DL-Methionine | 1 kg |
| Trace mineral premix*[2] | 1 kg |
| Zoalene 10% preparation (coccidiostat, trade name, made by Tanabe Seiyaku Co., Ltd.) | 1.25 kg |
| Compound 1 | 1 g |

Note:
*[1], *[2]: see Test 1.

The above ingredients were equally mixed to give an animal feed composition.

EXAMPLE 2

| Ingredient | |
| --- | --- |
| Skim milk | 270 kg |
| Dried whey | 100 kg |
| Fish meal | 50 kg |
| Wheat flour | 350 kg |
| Glucose | 50 kg |
| Tallow | 30 kg |
| Dried yeast | 100 kg |
| Starch | 21 kg |
| Casein sodium | 10 kg |
| Tricalcium phosphate | 10 kg |
| Sodium chloride | 4 kg |
| DL-Methionine | 500 g |
| Lysine hydrochloride | 1 kg |
| Vitamin A D$_3$E premix | 2 kg |
| Vitamin B premix*[1] | 2 kg |
| Trace mineral premix*[2] | 1 kg |
| Compound 1 | 1 g |

Note:
*[1], *[2]: see Test 1.

The above ingredients were equally mixed to give an animal feed composition (milk replacer).

EXAMPLE 3

| Ingredient | |
| --- | --- |
| Corn | 601 kg |
| Defatted soybean | 250 kg |
| Alfalfa meal | 20 kg |
| Fish meal | 80 kg |
| Plant oil | 25 kg |
| Calcium carbonate | 10 kg |
| Tricalcium phosphate | 5 kg |
| Sodium chloride | 3 kg |
| Vitamin A D$_3$ E premix | 1 kg |
| Vitamin B premix*[1] | 3 kg |
| DL-Methionine | 1 kg |
| Trace mineral premix*[2] | 1 kg |
| Zoalene 10% preparation (coccidiostat, trade name, made by Tanabe Seiyaku Co., Ltd.) | 1.25 kg |
| Compounds 2 or 3 | 1 g |

Note:
*[1], *[2]: see Test 1.

The above ingredients were equally mixed to give an animal feed composition.

EXAMPLE 4

| Ingredient | |
| --- | --- |
| Skim milk | 270 kg |
| Dried whey | 100 kg |
| Fish meal | 50 kg |
| Wheat flour | 350 kg |
| Glucose | 50 kg |
| Tallow | 30 kg |
| Dried yeast | 100 kg |
| Starch | 21 kg |
| Casein sodium | 10 kg |
| Tricalcium phosphate | 10 kg |
| Sodium chloride | 4 kg |
| DL-Methionine | 500 g |
| Lysine hydrochloride | 1 kg |
| Vitamin A D$_3$ E premix | 2 kg |
| Vitamin B premix*[1] | 2 kg |
| Trace mineral premix*[2] | 1 kg |
| Compound 2 | 1 g |

Note:
*[1], *[2]: see Test 1.

The above ingredients were equally mixed to give an animal feed composition (milk replacer).

We claim:

1. A growth promoting composition comprising:
   (a) an acyl peptide of the formula or its non-toxic salt:

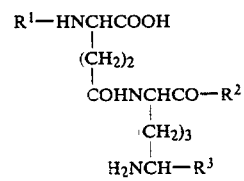

wherein
$R^1$ is lactoyl-alanyl-, $R^2$ is carboxymethylamino and $R^3$ is carboxy;
$R^1$ is heptanoyl, $R^2$ is 1-carboxyethylamino and $R^3$ is carboxy; or
$R^1$ is stearoyl, $R^2$ is 1-carboxyethylamino and $R^3$ is hydrogen, in an amount effective for promoting animal growth; and
   (b) a suitable animal feed.

2. A method of promoting the growth of animals comprising administering to said animals the acyl peptide of claim 1.

3. A method for promoting the growth of growing animals, which comprises orally administering to said animals the composition of claim 1.

4. A method of improving the rate of weight gain of growing animals, which comprises orally administering to said animals the composition of claim 1.

5. A method for improving the efficiency of feed utilization by growing animals, which comprises orally administering to said animals the composition of claim 1.

6. The composition according to claim 1, wherein the amount of the acyl peptide is 0.01 p.p.m. to 100 p.p.m.

7. The method according to claims 2, 3, 4 or 5, wherein the amount of the acyl peptide is 0.01 p.p.m. to 100 p.p.m.

8. The composition according to claim 1, wherein said animals are poultry or pigs.

9. The composition according to claim 8, wherein said poultry are chickens.

10. The method according to claims 2, 3, 4 or 5, wherein said animals are poultry or pigs.

11. The method according to claims 2, 3, 4 or 5, wherein said poultry are chickens.

12. The composition of claim 1, wherein the animal feed is in the form of a liquid feed, a dry feed or a pelleted feed.

13. The composition of claim 12, wherein the animal feed is selected from corn, rice, wheat, milo, soybean meal, wheat bran, defatted rice bran, fish meal, skim milk, dried whey, oils, fats and alfalfa meal.

14. The composition of claim 1, further comprising an additive selected from calcium carbonate, sodium chloride, choline chloride, vitamins and amino acids; minerals selected from magnesium sulfate, ferrous sulfate, copper sulfate, zinc sulfate, potassium iodide and cobalt iodide.

* * * * *